United States Patent [19]

Fischell et al.

[11] Patent Number: 5,059,166

[45] Date of Patent: Oct. 22, 1991

[54] INTRA-ARTERIAL STENT WITH THE CAPABILITY TO INHIBIT INTIMAL HYPERPLASIA

[75] Inventors: Robert E. Fischell, Dayton, Md.; Tim A. Fischell, Los Altos, Calif.

[73] Assignee: Medical Innovative Technologies R & D Limited Partnership, Dayton, Md.

[21] Appl. No.: 448,691

[22] Filed: Dec. 11, 1989

[51] Int. Cl.$^5$ ............................................. A61N 5/00
[52] U.S. Cl. ......................................... 600/3; 600/12; 606/108; 424/1.1
[58] Field of Search .................... 128/11, 804, 899; 600/1, 3, 12; 606/108, 139; 424/1.1

[56] References Cited

U.S. PATENT DOCUMENTS

| | | |
|---|---|---|
| 3,324,847 | 6/1967 | Zoumboulis ............................ 600/3 |
| 3,811,426 | 5/1974 | Culver et al. ............................ 600/3 |
| 3,927,325 | 12/1975 | Hungate et al. ........................ 600/3 |
| 4,496,435 | 8/1990 | Suthanthiran et al. ................. 600/3 |
| 4,584,991 | 4/1986 | Tokita et al. ............................ 600/3 |
| 4,768,507 | 9/1988 | Fischell et al. ..................... 606/108 |

Primary Examiner—Max Hindenburg
Assistant Examiner—Robin R. Longo

[57] ABSTRACT

Intra-arterial stents are frequently used subsequent to balloon angioplasty to maintain arterial patency. The most frequent cause for failure to maintain patency is the rapid growth of the injured arterial tissue through the openings in the stent, which rapid growth is called "intimal hyperplasia." Since irradiation from a radioisotope source is capable of selectively inhibiting the growth of hyperproliferating cells as compared with normal cells, a radioisotope material which forms part of the stent can be used to decrease the rate of arterial reclosure. The radioisotope could be placed inside the stent, alloyed into the metal from which the stent is made, or preferably, it can be coated onto the stent's exterior surface. Beta emitting radioisotopes having a half-life between 1 and 100 days would be best suited as a stent coating because of their comparatively short range of action within human tissue, and because of their comparatively short half-life. An anti-thrombogenic coating placed on the outer surface of the radioisotope stent would further reduce arterial reclosure by decreasing stent thrombogenicity.

11 Claims, 1 Drawing Sheet

INTRA-ARTERIAL STENT WITH THE CAPABILITY TO INHIBIT INTIMAL HYPERPLASIA

This invention is in the field of intra-arterial stents that are used to maintain patency of an arterial lumen typically subsequent to balloon angioplasty or atherectomy.

BACKGROUND OF THE INVENTION

Since the mid-to late-1980s, intra-arterial stents have found extensive use as a treatment to prevent restenosis subsequent to balloon angioplasty or atherectomy. A recurrent problem is that excessive tissue growth (intimal hyperplasia) at the site of the balloon dilation or atherectomy plaque excision results in restenosis of the artery. One possible solution to this problem is to coat the stent with an anti-thrombogenic surface so as to reduce platelet and fibrin deposition. This is described in U.S. Pat. No. 4,768,507 issued September 1988, to Robert E. Fischell and Tim A. Fischell entitled "Intravascular Stent and Percutaneous Insertion Catheter System for the Dilation of an Arterial Stenosis and the Prevention of Restenosis" which is incorporated herein by reference. Although an anti-thrombogenic coating can prevent acute thrombotic arterial closure and decrease the need for anticoagulent drug therapy, there is still an urgent need to decrease restenosis which is caused by intimal hyperplasia.

SUMMARY OF THE INVENTION

It is well known that radiation therapy can reduce the proliferation of rapidly growing cancer cells in a malignant tumor. The present invention utilizes a radioisotope which is integral to an arterial stent which can irradiate the tissue in close proximity to the implantation site of the stent in order to reduce the rapid tissue growth caused by arterial wall trauma resulting from balloon angioplasty or atherectomy.

DETAILED DESCRIPTION OF THE DRAWINGS

As described in U.S. Pat. No. 4,768,507, intra-arterial stents can be made in the form of a deployable helical coil spring. FIGS. 5 and 6 of the U.S. Pat. No. 4,768,507 illustrate typical cross sections of such a spring wire, helical coil stent.

Figure 1:
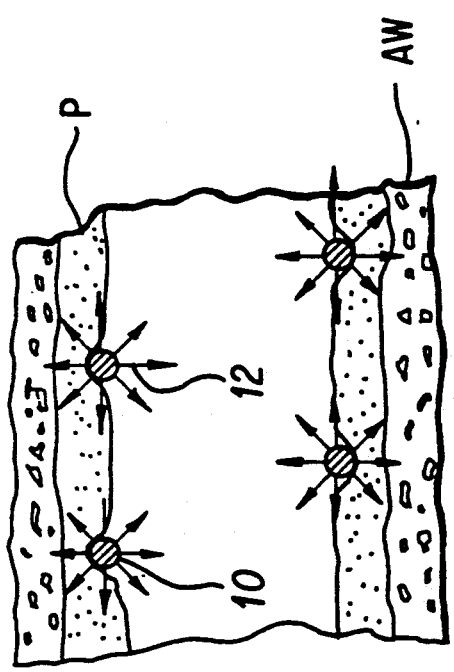
FIG. 1 is a cross section showing two turns of a radioisotope helical coil spring stent imbedded into a balloon dilated or atherectomized plaque within a human artery.

FIG. 1 of the present invention shows a cross section 10 of two turns of a helical coil spring stent that has been fabricated from a pure metal or alloy which has been irradiated so that it has become radioactive; i.e., it is a radioisotope. These two turns are shown imbedded into plaque P within the arterial wall AW. The arrows 12 pointing outward from the cross section 10 indicate the omnidirectional emission of particles from the stent wire. The purpose of this radiation is to decrease the rate of proliferative cell growth of the traumatized arterial wall AW (which growth is termed "intimal hyperplasia"). Thus it would be expected that restenosis, which frequently occurs after stent implantation, will be significantly reduced.

The radioisotope used for this purpose may be an alpha, beta or gamma emitter. The half-life would ideally be between 10 hours and 100 days. An optimum emitter might be a beta emitting isotope such as vanadium 48 which has a half-life of 16 days and only 8% of its emitted energy is from gamma radiation. The ideal attribute of a beta emitter is that the radiation does not travel very far in human tissue. Thus only the tissue in close proximity to the radioisotope stent will be affected. Furthermore only moderate levels of radiation are desired since it is known that very high levels can cause injury to nonproliferating tissues.

Another method to make the material of the stent spring wire is from a metal into which is alloyed an element that can be made into a radioisotope. For example, phosphorus 32, a 14.3 day half-life beta emitter, could be alloyed into steel which could be used for the stent wire.

Figure 2:
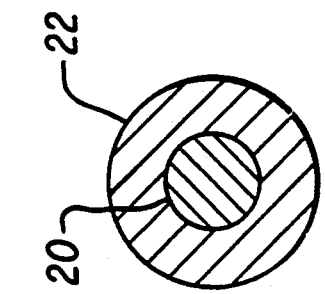
FIG. 2 is a cross section through the spring wire of a helical coil spring stent showing a radioisotope core material within a spring material.

FIG. 2 shows a stent wire cross section in which a wire made from a radioisotope core material 20 is formed within an outer covering 22 that has the attributes that are desirable for being a coil spring stent.

Figure 3:
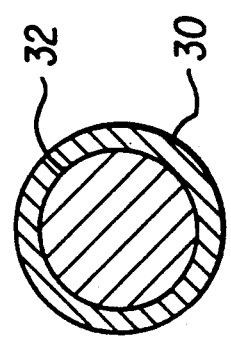
FIG. 3 is a cross section through the spring wire of a helical coil spring stent showing a thin plating of radioisotope material on the exterior surface.

FIG. 3 shows a cross section of an alternative embodiment of the present invention in which a radioisotope coating 30 is plated onto a spring material core 32. For example, the beta emitting isotope gold 198 (half-life 2.7 days) could be used to coat any suitable spring metal material.

Figure 4:
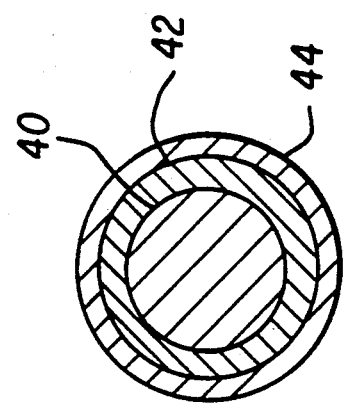
FIG. 4 is a cross section through a central core spring wire of a helical coil spring stent showing a radioisotope plating which is covered with an antithrombogenic coating.

FIG. 4 shows a more complex stent cross section in which a core 40 of some material ideally suited for stents is plated with a radioisotope coating 42 which is, in turn, coated with an anti-thrombogenic coating 42 such as carbon as described in U.S. Pat. No. 4,768,507.

Although helical coil spring stents have generally been described herein, the concept of utilizing a radioactive material within the stent structure so as to attenuate intimal hyperplasia is certainly applicable to any stent design. Furthermore, the temporary placement at the site of the vessel wall trauma of a radioactive source within the arterial lumen, for example a thin wire with a radioactive tip which wire can be withdrawn after a limited time is also envisioned.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. An intra-arterial stent comprising a generally tubular structure whose external surface is adapted to engage the arterial wall and which is patent throughout its entire interior length, said stent being formed from a radioactive material which is outwardly, radially expandable after percutaneous insertion into an artery, the radioactive material being adapted to be imbedded into the plaque so that the radioactive material preferentially emits radiation that can reduce the proliferation of cells in the arterial wall that are in close proximity to said stent.

2. The stent of claim 1 in which the radioactive material emitting the radiation is a radioisotope.

3. The stent of claim 2 in which said radioisotope is located within the structural material of said generally tubular structure of the stent.

4. The stent of claim 2 in which said radioisotope is plated onto said generally tubular structure of the stent.

5. The stent of claim 2 including an outer coating of anti-thrombogenic material.

6. The stent of claim 2 in which said radioisotope is a beta particle emitting radioisotope.

7. An intra-arterial stent comprising a generally tubular, thin-walled structure adapted to be expanded radially outward against the wall of an artery in a human body at least part of said stent being formed from a radioisotope material which is radially expandable, and said radioisotope material being adapted to be imbedded into the plaque within the arterial wall and further being adapted to decrease the rate of proliferative cell growth of the intimal cells.

8. The stent of claim 7 in which said radioisotope has a half-life of less than 100 days.

9. A method to decrease intimal hyperplasia caused by the treatment of an arterial stenosis the method comprising:

percutaneous insertion of a radioisotope source into an artery by means of a catheter so that it is positioned at the site of the arterial stenosis, said radioisotope source being formed from a plurality of thin, wire-like, interconnected, radially expandable parts in the form of an intra-arterial stent;

radially expanding the radioisotope source so that it becomes imbedded in the plaque within the arterial wall; and, removal of the catheter from the artery.

10. The method of claim 9 further comprising the step of dilating the stenosis by the use of a balloon angioplasty catheter prior to the insertion of the stent.

11. The method of claim 9 further comprising the step of excising at least some of the atheromatous plaque of the stenosis by means of an atherectomy catheter prior to the insertion of the stent.

* * * * *